(12) United States Patent
Um et al.

(10) Patent No.: US 10,975,448 B2
(45) Date of Patent: Apr. 13, 2021

(54) *CLOSTRIDIUM* SP. STRAIN PRODUCING HEXANOIC ACID IN HIGH YIELD AND METHOD FOR PRODUCING HEXANOIC ACID USING THE SAME

(71) Applicant: KOREA INSTITUTE OF SCIENCE AND TECHNOLOGY, Seoul (KR)

(72) Inventors: Youngsoon Um, Seoul (KR); Joongsuk Kim, Seoul (KR); Sun-Mi Lee, Seoul (KR); Gyeongtaek Gong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 16/253,581

(22) Filed: Jan. 22, 2019

(65) Prior Publication Data
US 2019/0226036 A1 Jul. 25, 2019

(30) Foreign Application Priority Data

Jan. 23, 2018 (KR) .................. 10-2018-0008361

(51) Int. Cl.
| | | |
|---|---|---|
| *C12R 1/145* | (2006.01) | |
| *C12P 7/52* | (2006.01) | |
| *C12P 7/16* | (2006.01) | |
| *C12P 7/40* | (2006.01) | |
| *C12P 7/04* | (2006.01) | |

(52) U.S. Cl.
CPC ............... *C12R 1/145* (2013.01); *C12P 7/04* (2013.01); *C12P 7/16* (2013.01); *C12P 7/40* (2013.01); *C12P 7/52* (2013.01)

(58) Field of Classification Search
CPC .... C12R 1/145; C12P 7/40; C12P 7/04; C12P 7/52; C12P 7/16; C12N 1/20
See application file for complete search history.

(56) References Cited

U.S. PATENT DOCUMENTS

| 9,359,611 B2 | 6/2016 | Koepke et al. |
| 2014/0024091 A1 | 1/2014 | Reed et al. |
| 2016/0215302 A1 | 7/2016 | Haas et al. |

FOREIGN PATENT DOCUMENTS

| KR | 2002-0033619 A | 5/2002 |
| KR | 10-2013-0056125 A | 5/2013 |
| KR | 10-2013-0077296 A | 7/2013 |
| KR | 10-1640325 B1 | 7/2016 |
| KR | 10-2016-0092931 A | 8/2016 |
| KR | 10-2016-0131236 A | 11/2016 |
| KR | 10-2016-0131237 A | 11/2016 |
| KR | 10-1745084 B1 | 6/2017 |
| WO | WO 00/68407 A1 | 11/2000 |

OTHER PUBLICATIONS

Ramachandriya et al., Applied Energy, 2013, vol. 112, p. 289-299.*
Ghasem D. Najafpour, in Biochemical Engineering and Biotechnology, 2007, Elsevier Science, Chapter 9—Material and Elemental Balance, p. 228-251.*
Wikipedia definition of "Invert or Inverted sugar" retrieved on Apr. 7, 2020, 8 pages of PDF.*
Fernández-Naveira et al., "Production of chemicals from C1 gases (CO, CO2) by Clostridium Carboxidivorans", World Journal of Microbiology and Biotechnology, Feb. 2017, pp. 33-43.
Jeon et al., "Production of hexanoic acid from D-galactitol by a newly isolated *Clostridium* sp. BS-1", Applied Microbiology and Biotechnology, vol. 88, Nov. 2010, pp. 1161-1167.
Kim et al., "C1 gases to hexanoic acid by a newly isolated strain *Clostridium* sp. JK1", 2017 KSBB Fall Meeting and International Symposium, Oct. 11-13, 2017, pp. 1-1502.
Phillips et al., "Butanol and hexanol production in Clostridium carboxidivorans syngas fermentation: Medium development and culture tebhniques", Bioresource Technology, vol. 190, 2015, pp. 114-121.

* cited by examiner

*Primary Examiner* — Kade Ariani
(74) *Attorney, Agent, or Firm* — Birch, Stewart, Kolasch & Birch, LLP

(57) ABSTRACT

The present disclosure relates to a *Clostridium* sp. JS66 strain producing metabolites having 4 to 6 carbon atoms in a high yield. The strain produces metabolites having 6 carbon atoms in a significantly high yield while reducing the production of acetic acid and ethanol as by-products.

17 Claims, 22 Drawing Sheets
Specification includes a Sequence Listing.

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Synthetic: primer 27F

<400> SEQUENCE: 1
agagtttgat ctgctcag                                       18

<210> SEQ ID NO 2
<211> LENGTH: 20
<212> TYPE: DNA
<213> ORGANISM: Artificial Sequence
<220> FEATURE:
<223> OTHER INFORMATION: Synthetic: primer 1492R

<400> SEQUENCE: 2
aaggaggtga tccagccgca                                     20

CLOSTRIDIUM SP. STRAIN PRODUCING HEXANOIC ACID IN HIGH YIELD AND METHOD FOR PRODUCING HEXANOIC ACID USING THE SAME

CROSS REFERENCE TO RELATED APPLICATIONS

This non-provisional application claims the benefit under 35 U.S.C. § 119(a) to Patent Application No. 10-2018-0008361, filed in the Republic of Korea on Jan. 23, 2018, all of which are hereby expressly incorporated by reference into the present application.

BACKGROUND OF THE INVENTION

Field of the Invention

Disclosed herein are a novel *Clostridium* sp. strain producing hexanoic acid in a high yield and a method for producing hexanoic acid using the same.

DESCRIPTION ABOUT NATIONAL SUPPORT RESEARCH AND DEVELOPMENT

This study is made by the support of the Climate change response technology development business of the National Research Foundation of Korea under the supervision of the Ministry of Science and ICT, and the subject name thereof is Development of biological production of n-C6 organic acids using by-product gas containing CO Subject Identification No.: 1711048841).

DESCRIPTION OF THE RELATED ART

The 2015 Paris climate change accord, signed by 195 countries around the world, clearly shows the efforts to reduce global greenhouse gases. The goal of the accord is to keep the average global temperature rise below 2° C. above pre-industrial levels. Scientific approaches to reduce carbon monoxide and carbon dioxide, which are main components of greenhouse gases, to keep up with this international trend have recently attracted attention even in the biorefinery industry.

Biological conversion methods that allow to consume both carbon monoxide and carbon dioxide utilize microorganisms using the Wood-Ljungdahl pathway. Most of the microorganisms that can grow using a mixed gas of carbon monoxide, carbon dioxide, and hydrogen as a substrate mainly produce acetic acid and ethanol, which have 2 carbon atoms, as their metabolites. However, a very few microorganisms produce medium-chain compounds having 6 carbon atoms from carbon monoxide and carbon dioxide, and their production pathways are shown in FIG. 1.

Among the compounds with 6 carbon atoms, hexanoic acid is colorless, has a cheese flavor, and is found in the fat of several animals. Hexanoic acid is a non-toxic medium-chain fatty acid. It is widely used as an additive for products such as foods, pharmaceuticals, and cosmetics due to its excellent absorption in the body. Hexanoic acid is used as a precursor of hexylphenol and hexyl derivatives, and the hexyl derivatives produced are also used as fragrances and food additives that give flavor. Among the hexyl derivatives, hexanol is a highly utilizable compound that can be used as an aircraft fuel additive.

Microorganisms known to produce hexanoic acid using a mixed gas of carbon monoxide, carbon dioxide, and hydrogen as a substrate include only the following two strains: *Clostridium carboxidivorans* and *Clostridium ragsdalei*. Therefore, in order to mass-produce hexanoic acid, it is necessary to find and develop a new strain that produces hexanoic acid in a high yield.

Among the fatty acids constituting natural fat, butyric acid is an organic acid having 4 carbon atoms. It is directly used as a raw material for making esters for synthetic fragrances, a calcium-removing agent for leather, a food additive in the dairy industry, and a therapeutic agent for cancer and gastrointestinal diseases. It is also widely used as a precursor of butanol and butyl-butyrate in the industries of chemicals, foods, pharmaceuticals, and the like. Currently, butyric acid is commercially produced by chemical processes such as synthesis via maleic anhydride or oxidation of butanol or propylene feedstock. However, considering the consumer's perception of compounds produced by chemical processes and environmental problems, it is necessary to produce it through a bioprocess.

*Clostridium tyrobutyricum* strain is one of the microorganisms known to produce butyric acid as a major fermentation product using glucose and xylose. However, its xylose utilization rate is lower than its glucose utilization rate. Also, it produces acetic acid as a by-product. Further, *Clostridium tyrobutyricum* can neither produce C6 compounds from sugars nor use a mixed gas of carbon monoxide, carbon dioxide and hydrogen as a substrate.

CITATION LIST

Patent Literature

Patent Literature 1: Korean Patent Application Publication No. 10-2016-0092931

Non-Patent Literature

Non-Patent Literature 1: Phillips, J. R., et al. (2015). "Butanol and hexanol production in *Clostridium carboxidivorans* syngas fermentation: Medium development and culture techniques." Bioresource Technology 190: 114-121.

Non-Patent Literature 2: Fernandez-Naveira, A A., et al. (2017). "Production of chemicals from C1 gases (CO, $CO_2$) by *Clostridium carboxidivorans*." World Journal of Microbiology and Biotechnology 33(3): 43.

SUMMARY OF THE INVENTION

In one aspect, an object of the present invention is to provide a novel *Clostridium* sp. strain producing metabolites having 6 carbon atoms in a significantly higher yield than conventional strains.

In one aspect, an object of the present invention is to provide a novel *Clostridium* sp. strain producing metabolites having 6 carbon atoms in a high yield not only in sugar-based metabolism but also when a carbon source other than sugars is used as a substrate.

In another aspect, an object of the present invention is to provide a novel *Clostridium* sp. strain producing metabolites having 6 carbon atoms in a high yield using a gas comprising at least one of carbon monoxide and carbon dioxide as a substrate.

In another aspect, an object of the present invention is to provide a method for producing metabolites having at least 4 carbon atoms using the novel strain.

In another aspect, an object of the present invention is to provide a method for producing metabolites having at least 4 carbon atoms using a mixed gas comprising at least one of carbon monoxide and carbon dioxide as a substrate.

In another aspect, an object of the present invention is to provide a method for producing metabolites having 6 carbon atoms in a high yield.

In another aspect, an object of the present invention is to provide a method for producing metabolites having at least 4 carbon atoms while reducing the production of acetic acid and ethanol as by-products.

In one aspect, the present invention provides a *Clostridium* sp. strain of accession No. KCTC 13355BP producing metabolites having 4 to 6 carbon atoms.

In another aspect, the present invention provides a method for producing metabolites having 4 to 6 carbon atoms, comprising supplying a substrate comprising a carbon source to a *Clostridium* sp. strain of accession No. KCTC13355BP to culture it.

In another aspect, the present invention provides a method for fixing greenhouse gases comprising carbon monoxide and carbon dioxide, steelworks by-product gases (including CO, $CO_2$, and $H_2$), and syngases using a *Clostridium* sp. JS66 strain.

DETAILED DESCRIPTION OF THE PREFERRED EMBODIMENTS

Figure 1:
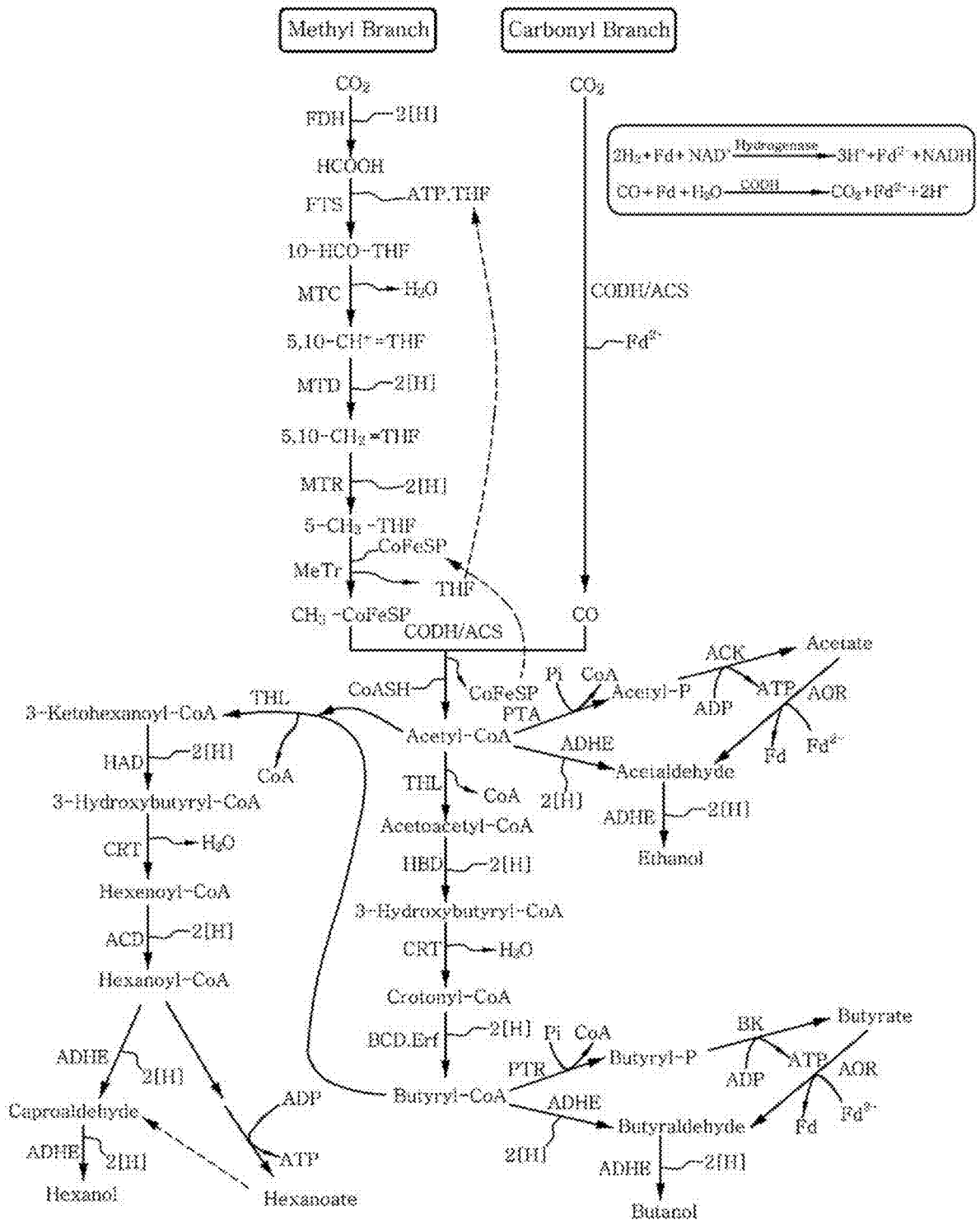
FIG. 1 is a diagram showing a metabolic pathway for producing hexanoic acid from a mixed gas of carbon monoxide, carbon dioxide, and hydrogen.

Hereinafter, embodiments of the present invention will be described in detail with reference to the accompanying drawings. This invention may, however, be embodied in many different forms and should not be construed as limited to the embodiments set forth herein. Rather, these embodiments are provided so that this disclosure will be thorough and complete and fully convey the spirit of the invention to those skilled in the art. The width, thickness, etc. of the elements in the drawings may be slightly exaggerated in order to clearly illustrate each element. In addition, only part of the elements may be illustrated for convenience of explanation. However, those skilled in the art could easily conceive the rest of the elements. Also, those skilled in the art could embody the spirit of the present invention in various other forms without departing from the spirit of the invention.

According to one embodiment, the present invention provides a *Clostridium* sp. strain producing metabolites having at least 4 carbon atoms.

The strain is a *Clostridium* sp. JS66 strain of accession No. KCTC13355BP, *Clostridium* sp. The *Clostridium* sp. JS66 strain is a novel strain isolated and identified as capable of producing metabolites having 6 carbon atoms in a high yield, and was granted the accession number KCTC13355BP on Sep. 19, 2017.

Strains belonging to *Clostridium* sp. are gram-positive bacilli with peritrichous flagellum, and most of them are obligate anaerobic bacteria. They form endospores, but the morphology and location thereof differ depending on the bacteria.

The *Clostridium* sp. JS66 according to this embodiment is an obligate anaerobic bacterium and generally produces acetic acid, butyric acid, hexanoic acid, ethanol, butanol, and hexanol as the metabolites. When cultured using glucose as the substrate, it mainly produces acetic acid, butyric acid, and hexanoic acid. When cultured using a mixed gas of carbon monoxide, carbon dioxide, and hydrogen as the substrate, it produces all of these six compounds.

The optimal culture temperature of the *Clostridium* sp. JS66 may be 25 to 30° C., for example 30° C.

In one embodiment, metabolites having 4 to 6 carbon atoms can be produced at the same time, and compounds having 6 carbon atoms can be produced in a high yield. The metabolites having 4 to 6 carbon atoms may include, for example, at least one of butyric acid, hexanoic acid, hexanol, and butanol.

Butyric acid may be represented by the formula $C_4H_8O_2$, and the chemical structure thereof is as follows:

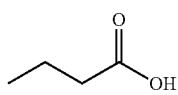

Formula 1

Hexanoic acid may be represented by the formula $C_5H_{11}COOH$, and the chemical structure thereof is as follows:

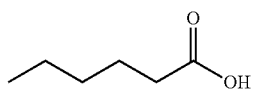

Formula 2

Hexanol may be represented by the formula $C_6H_{13}OH$.
Butanol may be represented by the formula $C_4H_9OH$.

In one embodiment, the *Clostridium* sp. JS66 produces metabolites having 4 to 6 carbon atoms at the same time using a substrate comprising a sugar, and particularly can produce metabolites having 6 carbon atoms in a high yield.

In one embodiment, the sugar may include all sugars that can be used as a general carbon source and are capable of growing microorganisms, such as hexoses such as glucose, fructose, and galactose, pentoses such as xylose, arabinose, and mannose, and disaccharides such as cellobiose and sucrose.

In one embodiment, when a substrate comprising the sugar is used, the *Clostridium* sp. JS66 can produce butanol and butyric acid simultaneously with metabolites having 6 carbon atoms.

In one embodiment, when a substrate comprising the sugar is used, the *Clostridium* sp. JS66 can produce hexanoic acid in a high yield. The yield of hexanoic acid may be, for example, at least 0.20 g/g sugar.

In one embodiment, the *Clostridium* sp. JS66 can produce metabolites having 4 to 6 carbon atoms at the same time using a gas comprising a carbon source as a substrate. In one embodiment, the *Clostridium* sp. JS66 can produce metabolites having 6 carbon atoms in a high yield.

The gas comprising a carbon source may comprise at least one of carbon monoxide and carbon dioxide. For example, the gas may be a mixed gas further comprising hydrogen.

In one embodiment, the gas comprising a carbon source may include, for example, carbon monoxide alone, a mixed gas of carbon monoxide and hydrogen, a mixed gas of carbon dioxide and hydrogen, or a mixed gas of carbon monoxide, carbon dioxide, and hydrogen.

While it is known that acetic acid is mainly produced as a result of the metabolism of microorganisms using the gas comprising a carbon source as described above, the *Clostridium* sp. JS66 according to this embodiment can produce metabolites having 4 to 6 carbon atoms at the same time using a gas comprising a carbon source, and particularly can produce metabolites having 6 carbon atoms in a high yield.

In one embodiment, the *Clostridium* sp. JS66 strain can produce butyric acid in a yield of at least 0.1 g/g CO using the gas comprising a carbon source.

In one embodiment, the *Clostridium* sp. JS66 strain can produce hexanoic acid in a yield of at least 0.05 g/g CO using the gas comprising a carbon source.

With regard to the yield of hexanoic acid, the expression "high yield" means that the amount of the hexanoic acid produced during the culture of a microorganism relative to the amount of the carbon monoxide consumed is closest to the theoretical yield that can be obtained from the Wood-Ljungdahl pathway of 0.259 g/g CO. In one embodiment, the yield may be 0.05 g/g CO to 0.259 g/g CO, for example, 0.05 g/g CO to 0.20 g/g CO, and for example, 0.19 g/g CO.

In one embodiment, the *Clostridium* sp. JS66 strain can produce hexanol in a yield of at least 0.003 g/g CO using the gas comprising a carbon source.

In one embodiment, when the gas comprising a carbon source is a mixed gas comprising carbon monoxide and carbon dioxide, the volume ratio of carbon monoxide and carbon dioxide may be 1:99 to 99:1, for example, 3 to 7:1 to 3 or 1:1.

In one embodiment, when the mixed gas is a mixed gas comprising carbon monoxide and hydrogen, the volume ratio of carbon monoxide and hydrogen may be 1:99 to 99:1, for example, 3 to 7:2 to 4 or 3:4.

In one embodiment, when the mixed gas is a mixed gas comprising carbon dioxide and hydrogen, the volume ratio of carbon dioxide and hydrogen may be 1:99 to 99:1, for example, 1 to 3:2 to 4 or 3:4.

In one embodiment, the mixed gas may comprise carbon monoxide, carbon dioxide, and hydrogen in a volume ratio of 3 to 7:1 to 3:2 to 4, for example, 3:3:4.

In one embodiment, the volume ratio of the mixed gas may be adjusted in consideration of reaction time, yield, etc. For example, if the ratio of carbon monoxide increases, the lag phase may increase due to CO inhibition, but the yield of metabolites having 4 to 6 carbon atoms may increase.

According to one embodiment, the present invention provides a method for producing metabolites having 4 to 6 carbon atoms using a *Clostridium* sp. JS66 strain of accession No. KCTC 13355BP. The strain and metabolites are as described for the *Clostridium* sp. strain producing metabolites having 4 to 6 carbon atoms, and thus a description thereof will be omitted.

The method may comprise supplying *Clostridium* sp. JS66 strain of accession No. KCTC13355BP to a substrate comprising a carbon source and culturing the strain.

The substrate comprising a carbon source may comprise at least one of a sugar and a gas comprising a carbon source. The substrate is as described above, and thus a detailed description thereof will be omitted.

In order to improve the yield, the culture may be carried out at 25° C. or more, 26° C. or more, 27° C. or more, 28° C. or more, or 29° C. or more and 33° C. or less, 32° C. or less, 31° C. or less, or 30° C. or less. For example, the culture may be carried out at a temperature of 30° C.

The culture may be carried out at an initial pH of 5 to 8, for example, an initial pH of 5.5 to 7. The pH changes with the progress of the culture.

The culture may be carried out under anaerobic conditions. As used herein, the term "anaerobic condition" refers to an environment in which the amount of oxygen is small to an extent that an obligate anaerobic microorganism can survive or oxygen is not present.

In one embodiment, when the substrate is a gas comprising a carbon source, the culture may be carried out at an initial total gas pressure of 3 bar or less, for example, 0.5 to 2 bar, for example, 1.5 bar, although not limited thereto.

In one embodiment, the culture may be carried out in a medium containing yeast extract. In order to improve the yield, the medium may contain 0.1 g/L to 10 g/L, for example, 0.5 g/L to 2 g/L, of yeast extract.

In one embodiment, the culture may be carried out in a medium containing molybdenum and tungsten, which are known to be necessary for microbial gas culture. For example, the culture may be carried out in a medium containing at least one of yeast extract, MES (2-N-morpholino ethane sulfonic acid), potassium hydroxide (KOH), ammonium chloride ($NH_4Cl$), calcium chloride dihydrate ($CaCl_2 2 H_2O$), magnesium sulfate heptahydrate ($MgSO_4 7H_2O$), sodium chloride (NaCl), potassium chloride (KCl), potassium phosphate ($KH_2PO_4$), potassium phosphate dibasic ($K_2HPO_4$), cysteine hydrochloride (HCl-cysteine), nitrilotriacetic acid, manganese sulfate hydrate ($MnSO_4H_2O$), ammonium sulfate (($NH_4$)$_2SO_4$), ferrous sulfate heptahydrate ($FeSO_4 7H_2O$), ammonium ferrous sulfate hexahydrate ($Fe(SO_4)_2(NH_4)_2 6H_2O$), cobalt chloride hexahydrate ($CoCl_2 6H_2O$), zinc sulfate heptahydrate ($ZnSO_4 7H_2O$), copper chloride dihydrate ($CuCl_2 2H_2O$), nickel chloride dihydrate ($NiCl_2 2H_2O$), sodium molybdate dihydrate ($Na_2MoO_4 2H_2O$), sodium tungstate ($Na_2WO_4$), aluminum potassium sulfate dodecahydrate ($KAl(SO_4)_2 12H_2O$), and boric acid ($H_3BO_3$). For example, the culture may be carried out in a medium containing yeast extract.

In one embodiment, the method may further comprise, before the culture, the step of seed culture in a medium containing glucose. The medium used for the seed culture may contain, for example, 1 g/L to 10 g/L, for example 5 g/L, of glucose.

According to one embodiment, the present invention may provide a method for fixing greenhouse gases, steelworks by-product gases (including CO, $CO_2$ and $H_2$), and syn-gases.

In this embodiment, the method may comprise supplying Clostridium sp. JS66 strain of accession No. KCTC13355BP to a mixed gas comprising carbon monoxide and carbon dioxide to culture the strain.

The use of the strain allows to effectively fix greenhouse gases comprising carbon monoxide and carbon dioxide, steelworks by-product gases (including CO, $CO_2$ and $H_2$), and syngases and thereby to produce useful compounds.

The specific method according to this embodiment is as described for the method for producing metabolites having 4 to 6 carbon atoms using a Clostridium sp. JS66 strain of accession No. KCTC13355BP according to one embodiment of the present invention as described above, and thus a description thereof will be omitted.

Hereinafter, the present invention will be described in more detail with reference to examples, comparative examples and test examples. However, it will be apparent to those skilled in the art that the following examples are provided for illustrative purposes only to describe the present invention more specifically, and the scope of the present invention is not limited thereto.

Test Example 1: Isolation of a Clostridium sp. JS66 Strain

Samples were collected from the soil of the tidal flat (37°37'15.8"N 126°32'24.7"E) of Hwangsando in Choji-ri, Gilsang-myeon, Ganghwa-gun, Incheon under anaerobic conditions in around September 2016. The collected samples were repeatedly cultured under anaerobic conditions at 30° C. using a mixed gas of carbon monoxide, carbon dioxide, and hydrogen as a substrate to screen strains capable of growing using a mixed gas comprising carbon monoxide and carbon dioxide as a substrate. Tables 1 and 2 show the medium composition used to screen the target strains from environmental samples.

TABLE 1

| Medium composition | g/L |
|---|---|
| Yeast extract | 0.5 |
| MES (2-N-morpholino ethane sulfonic acid) | 10 |
| KOH | 1.165 |
| $NH_4Cl$ | 2 |
| $CaCl_2 2H_2O$ | 0.08 |
| $MgSO_4 7H_2O$ | 0.4 |
| KCl | 0.2 |
| $KH_2PO_4$ | 0.2 |
| Resazurin | 0.01 |
| HCl-cysteine | 0.2 |
| Trace elements | 1 ml |

TABLE 2

| Trace elements | mg/L |
|---|---|
| Nitrilotriacetic acid | 20 |
| $MnSO_4H_2O$ | 20 |
| $Fe(SO_2)_2(NH_4)_2 6H_2O$ | 8 |
| $CoCl_2 6H_2O$ | 2 |
| $ZnSO_4 7H_2O$ | 0.002 |
| $CuCl_2 2H_2O$ | 0.2 |
| $NiCl_2 2H_2O$ | 0.2 |
| $Na_2MoO_4 2H_2O$ | 2.2 |
| $Na_2WO_4$ | 0.2 |
| $KAl(SO_4)_2 12H_2O$ | 0.2 |
| $H_3BO_3$ | 0.1 |

As a result of the isolation of strains, a strain was found which produces about 0.2 g/L of hexanoic acid using a mixed gas comprising carbon monoxide, carbon dioxide, and hydrogen in volume percentages of 30%, 30%, and 40%, respectively, under the total gas pressure of 1.5 bar and which produces about 1 g/L of hexanoic acid when 5 g/L of glucose is supplied without the use of a mixed gas. As a result of 16s rDNA sequencing analysis, the strain was found to belong to Clostridium sp. The isolated strain was stored in 25% glycerol at −70° C.

Test Example 2: 16s rDNA Gene Sequence and Phylogenetic-Systematic Characteristics Genomic DNA was extracted from the hexanoic acid-producing strain screened in Test Example 1 above. Using this as the template, 16s rDNA gene was amplified by PCR. The primers used for PCR amplification were 27F (5'-AGAGTTTGATCTGCTCAG-3'; SEQ ID NO: 1) and 1492R (5'-AAGGAGGTGATCCAGCCGCA-3'; SEQ ID NO: 2). The PCR consisted of 30 cycles of 98° C. for 3 minutes, 98° C. for 20 seconds, 54° C. for 20 seconds, and 72° C. for 20 seconds, followed by reaction at 72° C. for 5 minutes. The amplified 16s rDNA gene product was subjected to sequencing analysis by Macrogen, Inc. As a result, 1146 arbitrary base sequences were obtained. Basic Local Alignment Search Tool (BLAST) was used to compare these sequences with GenBank data. As a result of comparing the 16s rDNA sequences of bacteria with a high similarity to these base sequences, *Clostridium carboxidivorans*, which showed similarity of 99% or more to the isolated JS66 strain, was found to have the highest degree of similarity. However, *Clostridium ljungdahlii* and *Clostridium autoethanogenum* are 100% identical in 16s rDNA although they are different strains from each other. Thus, these two strains are distinguished from each other by the difference of phenotype, not by the difference of genotype. Therefore, the difference in phenotype was evaluated between the isolated *Clostridium* sp. JS66 strain and *Clostridium carboxidivorans* strain.

Figure 2:
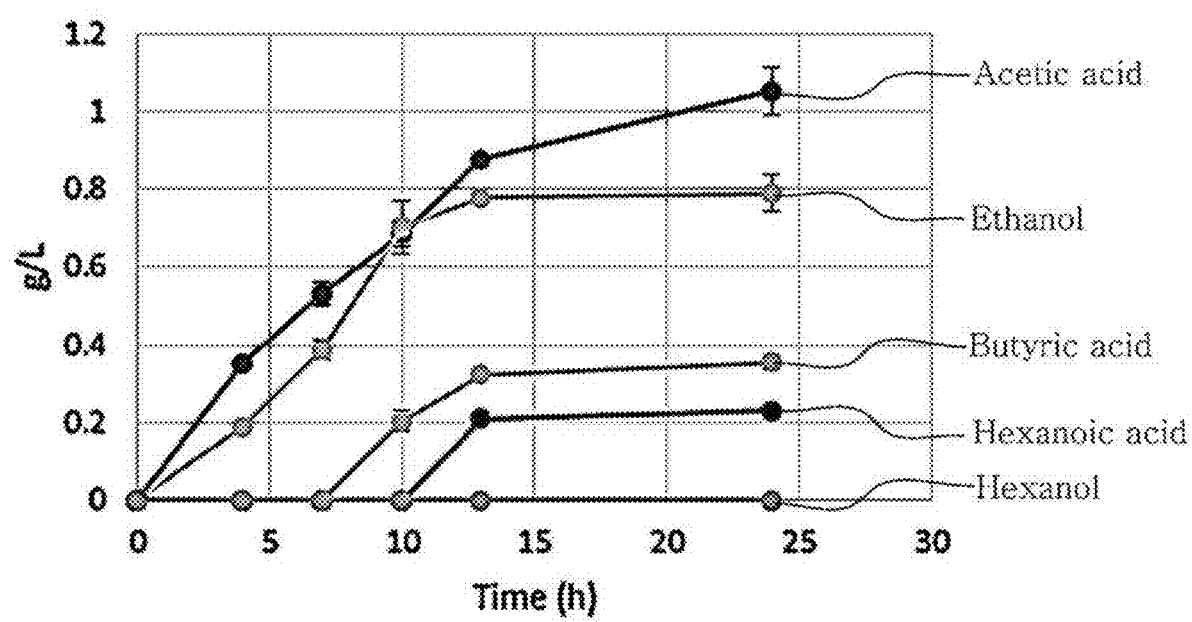
FIG. 2 is a graph showing the product of metabolism of *Clostridium carboxidivorans* using 5 g/L of glucose as a substrate.
Figure 3:
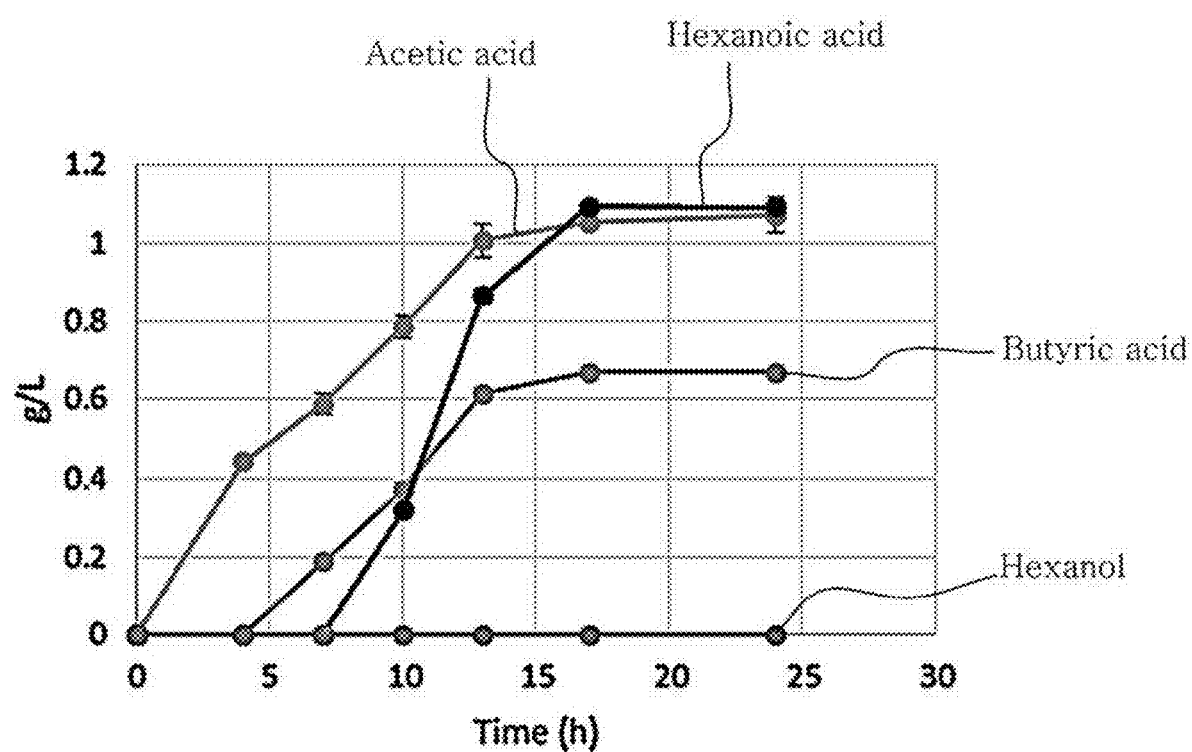
FIG. 3 is a graph showing the product of metabolism of *Clostridium* sp. JS66 using 5 g/L of glucose as a substrate.
Figure 4:
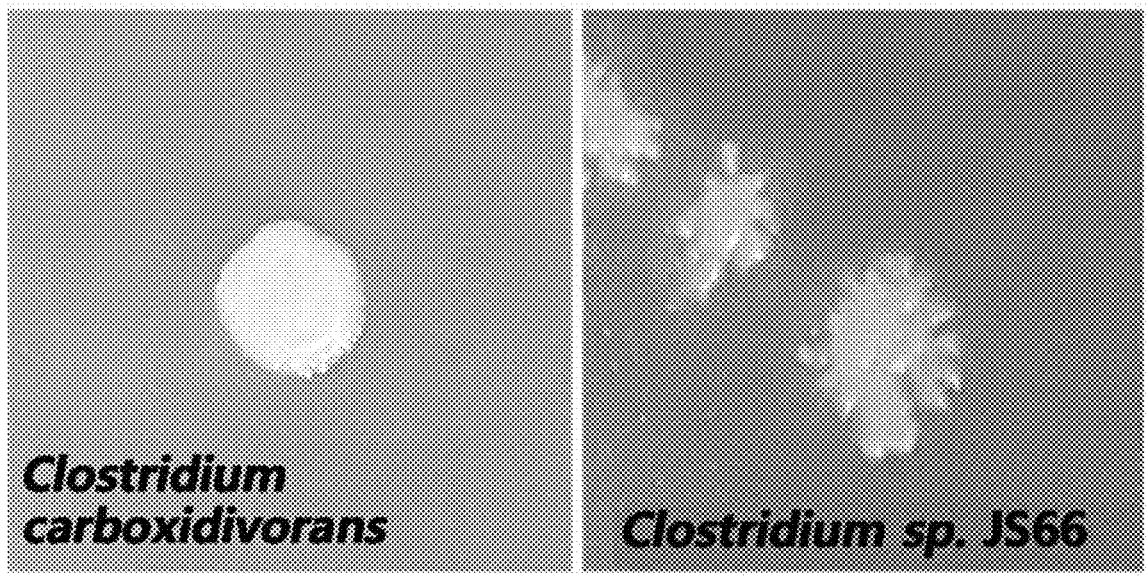
FIG. 4 is a photograph showing the morphological differences of colonies of *Clostridium* sp. JS66 and *Clostridium carboxidivorans*.
Figure 5:
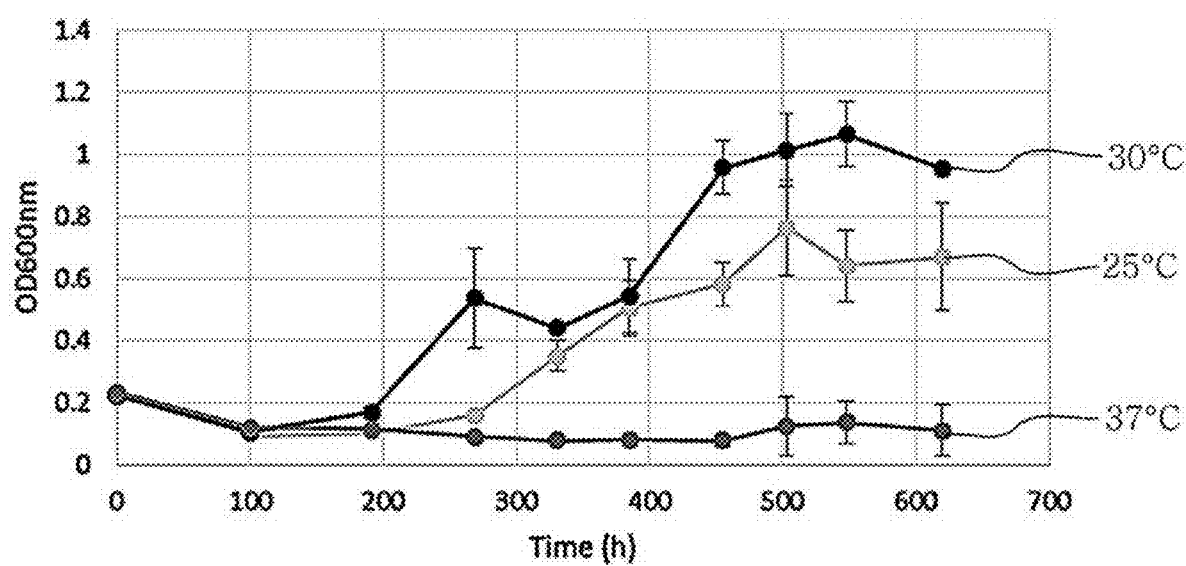
FIG. 5 is a graph showing the growth of *Clostridium* sp. JS66 in culture using a gas at different temperatures of 25° C., 30° C., and 37° C. with the medium composition used to isolate the strain from environmental samples.
Figure 6:
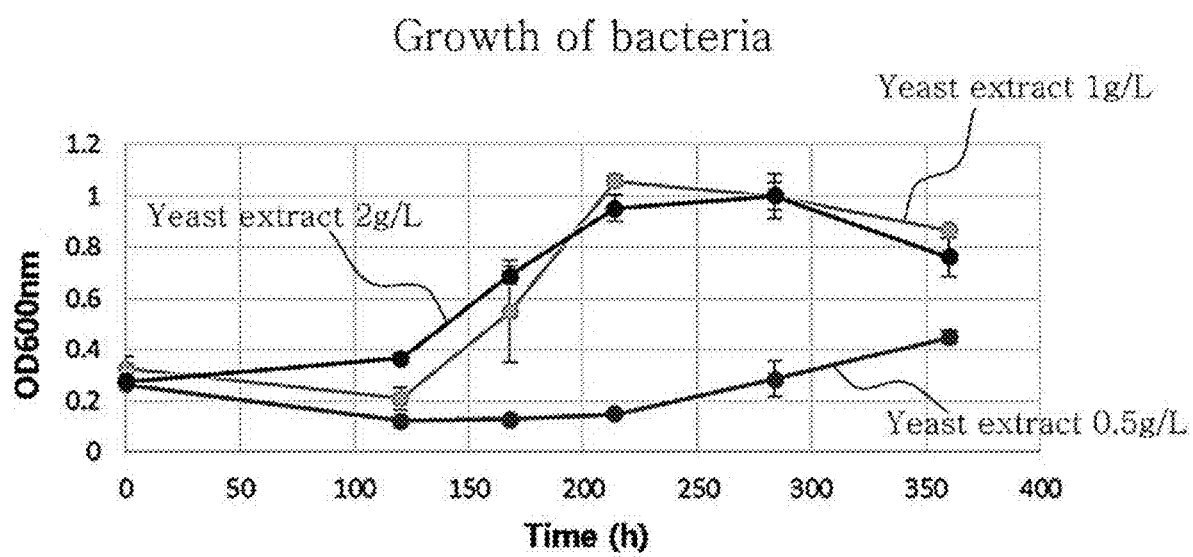
FIG. 6 is a graph showing growth changes in the culture of *Clostridium* sp. JS66 bacteria using a gas with varying the concentrations of yeast extract in the medium.
Figure 7:
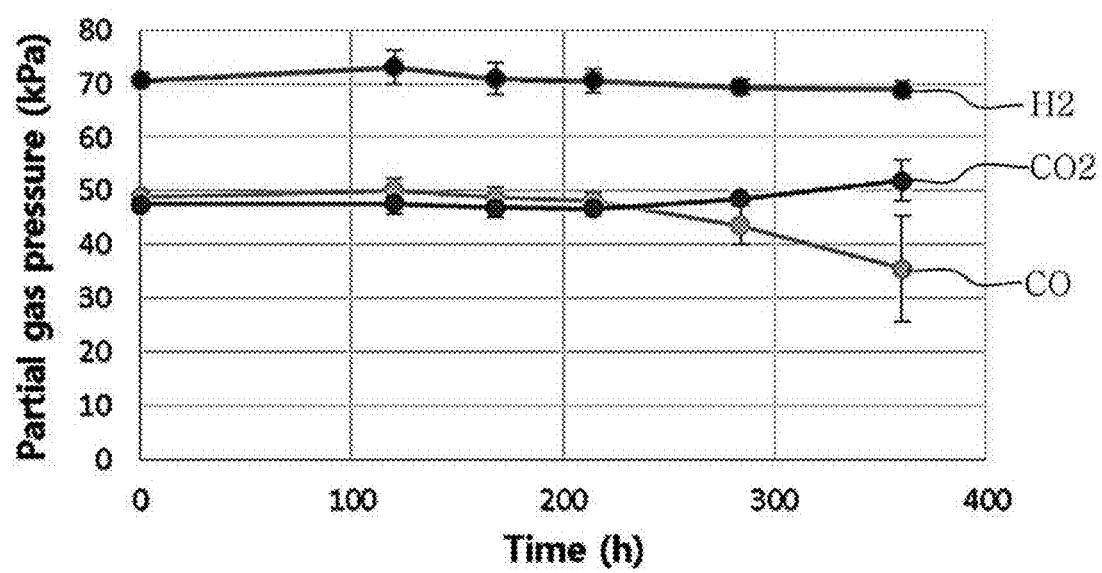
FIG. 7 is a graph showing changes in partial gas pressure in the culture of *Clostridium* sp. JS66 using a gas at the concentration of yeast extract in the medium of 0.5 g/L.
Figure 8:
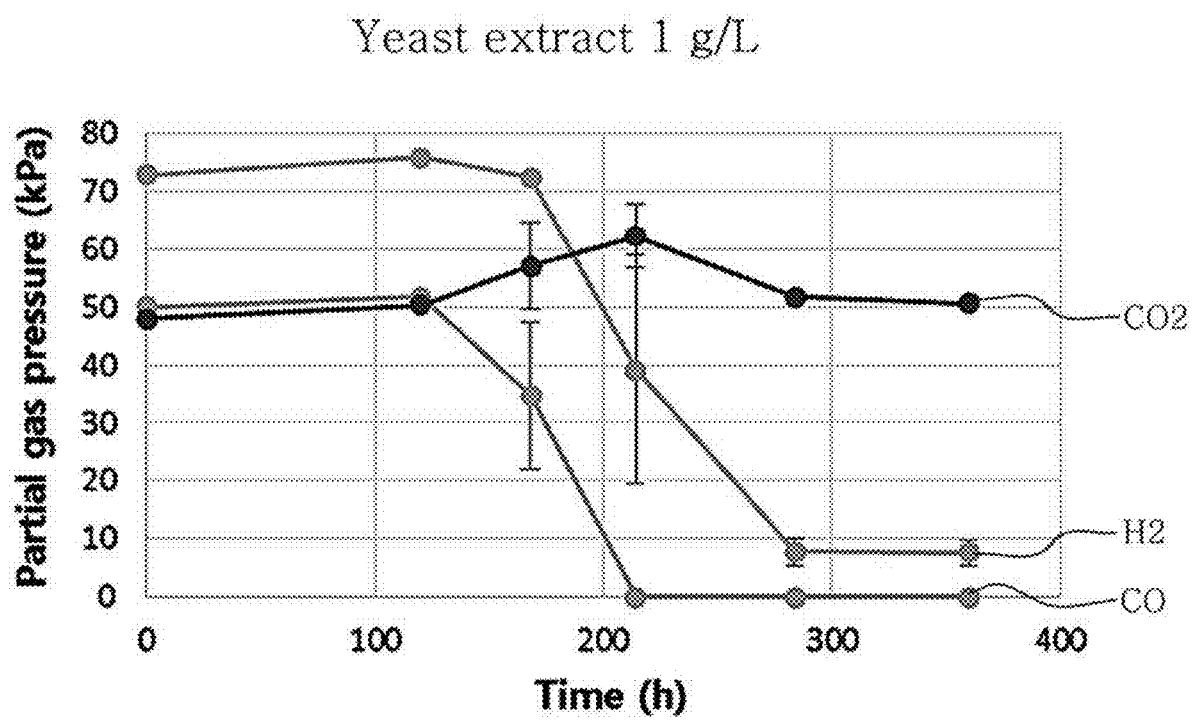
FIG. 8 is a graph showing changes in partial gas pressures in the culture of *Clostridium* sp. JS66 using a gas at the concentration of yeast extract in the medium of 1 g/L.
Figure 9:
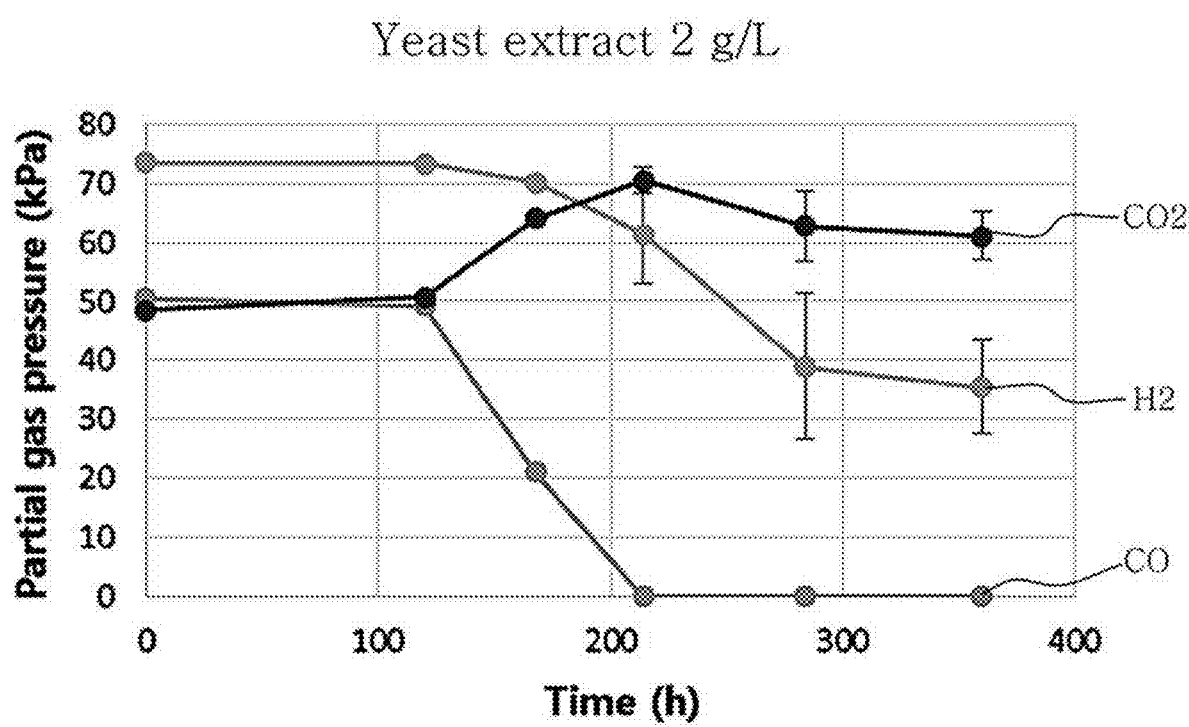
FIG. 9 is a graph showing changes in partial gas pressures in the culture of *Clostridium* sp. JS66 using a gas at the concentration of yeast extract in the medium of 2 g/L.

When cultured using glucose, *Clostridium* sp. JS66 strains and *Clostridium carboxidivorans* strains are different from each other in their metabolites, which is illustrated in FIG. 2 and FIG. 3. In the case of using 5 g/L of glucose, the *Clostridium* sp. JS66 strain isolated did not produce ethanol as a metabolite, unlike *Clostridium carboxidivorans* strains, and produced about five times as much hexanoic acid and about twice as much butyric acid as *Clostridium carboxidivorans*. The composition of the medium containing 5 g/L of glucose is shown in Table 3. *Clostridium* sp. JS66 strains differ from *Clostridium carboxidivorans* strains in that *Clostridium* sp. JS66 strains have a heterogeneous colony morphology whereas *Clostridium carboxidivorans* strains have a circular colony morphology, which is illustrated in FIG. 4. Unlike *Clostridium carboxidivorans* strains, which exhibited optimal growth in culture using a gas (carbon monoxide, carbon dioxide, and hydrogen in the volume percentages of 30%, 30%, and 40%, respectively) at the temperature condition of 37° C. and the medium composition of Table 1 and Table 2, the *Clostridium* sp. JS66 strain, isolated at 30° C., could not grow at 37° C., which is shown in FIG. 5.

Whole genome sequencing was performed by ChunLab Inc. and the genome analysis results showed that *Clostridium* sp. JS66 had a genome size of 6.3 Mbp, and *Clostridium carboxidivorans* P7 had a genome size of 5.7 Mbp, demonstrating that they differ in genome size. Average nucleotide identity (ANI) values were calculated at https://www.ezbiocloud.net/tools/ani. As a result of comparing *Clostridium* sp. JS66 with *Clostridium carboxidivorans* P7, the ANI value between them was found to be 95.5%. In order to determine whether *Clostridium* sp. JS66 is a novel microorganism different from *Clostridium carboxidivorans* P7, DNA-DNA hybridization experiment was carried out by Sellusone Co., Ltd. As a result, the DNA-DNA hybridization value between the strains was found to be 33%. If the DNA-DNA hybridization value between strains is 70% or less, the strain at issue is classified as a new species. Therefore, the isolated *Clostridium* sp. JS66 is classified as a new species.

Test Example 3: Culture Medium and Analysis Conditions

Experiments in the following test examples were carried out using the following media and analysis conditions.

(1) Used Medium

For the production of hexanoic acid by a *Clostridium* sp. JS66 strain, a medium having the composition of Table 1 and Table 2, which was used for isolating the strain, was used. The strain was cultured using a mixed gas of carbon monoxide, carbon dioxide, and hydrogen in the volume percentages of 30%, 30% and 40%, respectively, as the substrate under the total gas pressure of 1.5 bar. The strain was seed-cultured in a medium containing 5 g/L of glucose and which has the composition shown in Table 3, followed by washing once and a main culture in a medium having the composition shown in Table 1 and Table 2. The inoculum was inoculated at about 10%, and the experiment was conducted with stirring at 150 rpm.

TABLE 3

| Medium composition | g/L |
|---|---|
| Glucose | 5 |
| $K_2HPO_4$ | 0.5 |
| $KH_2PO_4$ | 0.5 |
| $(NH_4)_2SO_4$ | 2 |
| $MnSO_4H_2O$ | 0.01 |
| $MgSO_47H_2O$ | 0.2 |
| $FeSO_47H_2O$ | 0.01 |
| NaCl | 0.01 |
| Yeast extract | 6 |
| MES | 19.52 |

KOH adjust pH 6.0

(2) Analysis Method

The growth of the strain was measured by optical density (OD) at 600 nm using a UV-spectrophotometer (Cary 60, Agilent Technologies, CA, USA). The partial gas pressures of carbon monoxide, carbon dioxide, and hydrogen were analyzed using gas chromatography (Agilent Technologies 6890N, CA, USA) equipped with a thermal conductivity detector (TCD). Porepack Q was used as the column with the inlet temperature of 100° C. and the detector temperature of 200° C. The mobile phase argon gas was fed at 15.5 ml/min at 50° C. Ethanol, butanol, hexanol, and hexanoic acid were analyzed using gas chromatography (Agilent Technologies 6890N, CA, USA) equipped with a flame ionization detector (FID). HP-Innowax (Agilent, 30 m×0.32 mm×0.25 μm) was used as the column with the inlet temperature of 250° C. and the detector temperature of 250° C. The oven temperature was increased from 50° C. by 10° C./min to the final temperature of 250° C. Helium gas was used as the mobile phase and the inlet pressure was maintained at 9.41 psi. Acetic acid and butyric acid were analyzed using liquid chromatography (Agilent Technologies 1260 infinity, CA, USA) equipped with a UV detector. HI-PLEX H (300×7.7 mm) column was used as the column with the column temperature of 65° C. 5 mM sulfuric acid was used as the mobile phase and the flow rate was 0.6 mL/min. The UV wavelength of the detector for organic acid detection was 210 nm.

Test Example 4: Growth and Metabolite Production of *Clostridium* sp. JS66 Strain Depending on the Concentration of Yeast Extract

*Clostridium* sp. JS66 strain was cultured at 30° C. under the conditions of Test Example 3 and in the culture medium of the composition of Table 1 and Table 2, with varying the concentration of yeast extract as shown in Table 4 below. Changes in the growth of the strain, partial gas pressures, and in the yield of metabolites having at least 4 carbon atoms were identified, and the results are shown in FIG. 6 to FIG. 10.

TABLE 4

| Yeast extract (g/L) | 0.5 | 1 | 2 |
|---|---|---|---|
| Time at the maximum concentration of hexanoic acid (hour) | — | 284 | 284 |
| pH at the maximum concentration of hexanoic acid | — | 4.62 | 4.95 |
| OD 600 nm value at the maximum concentration of hexanoic acid | — | 1.05 | 0.95 |
| Maximum concentration of hexanoic acid (g/L) | nd | 0.19 | 0.08 |
| Acetic acid (g/L) | — | 2.89 | 2.68 |
| Butyric acid (g/L) | — | 0.69 | 0.40 |
| Ethanol (g/L) | — | 0.36 | 0.42 |
| Butanol (g/L) | — | 0.10 | 0.07 |
| Hexanol (g/L) | — | nd | nd |
| Yield of hexanoic acid (g/g CO) | — | 0.04 | 0.02 |

Figure 10:
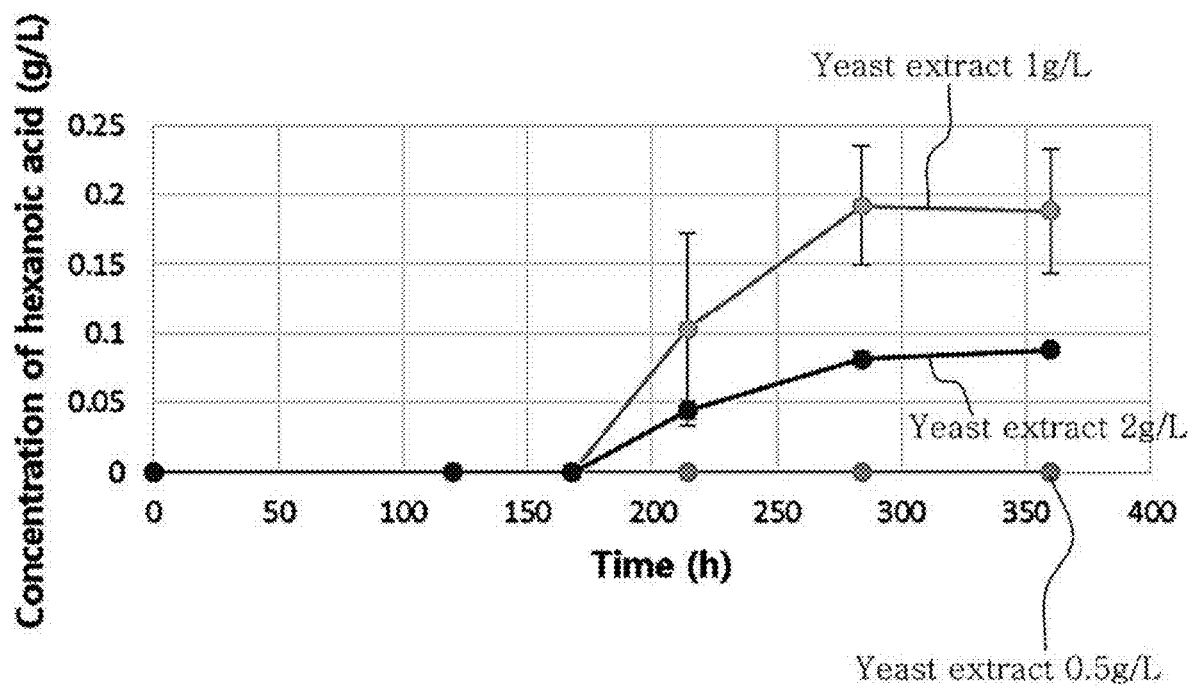
FIG. 10 is a graph showing changes in the yield of hexanoic acid in the culture of *Clostridium* sp. JS66 using a gas with varying the concentration of yeast extract in the medium.
Figure 11:
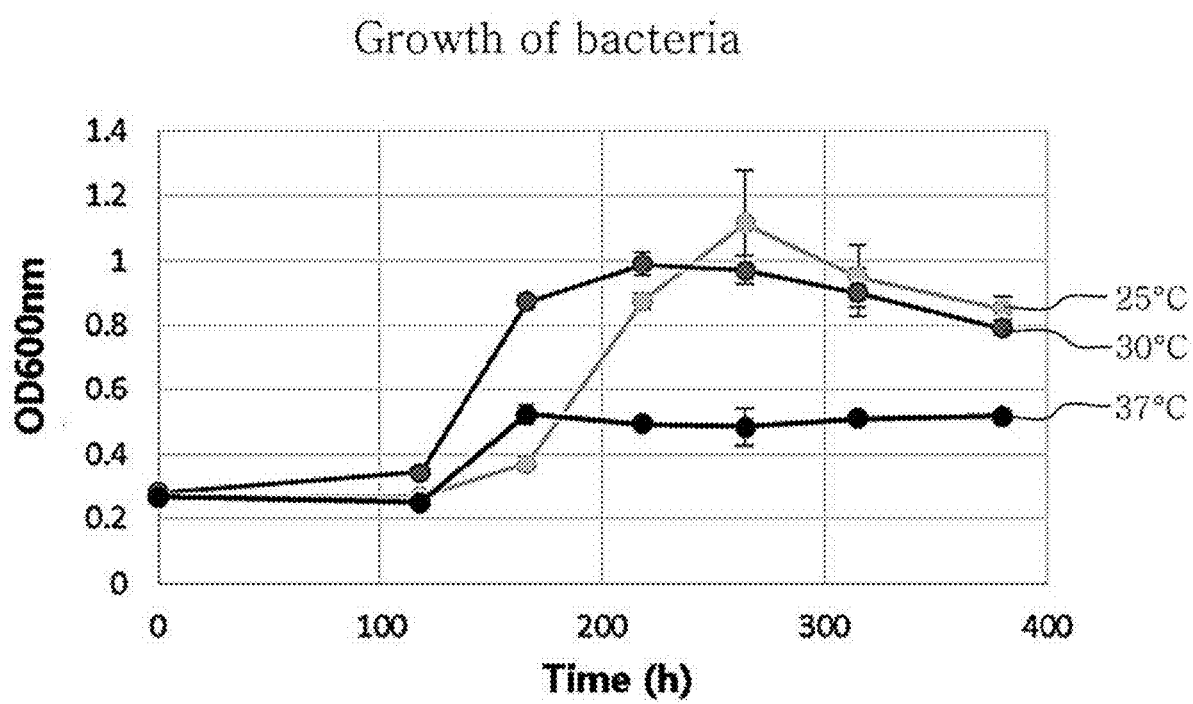
FIG. 11 is a graph showing the growth of *Clostridium* sp. JS66 bacteria when cultured with a gas at different temperatures of 25° C., 30° C., and 37° C. and the concentration of yeast extract in the medium of 1 g/L.
Figure 12:
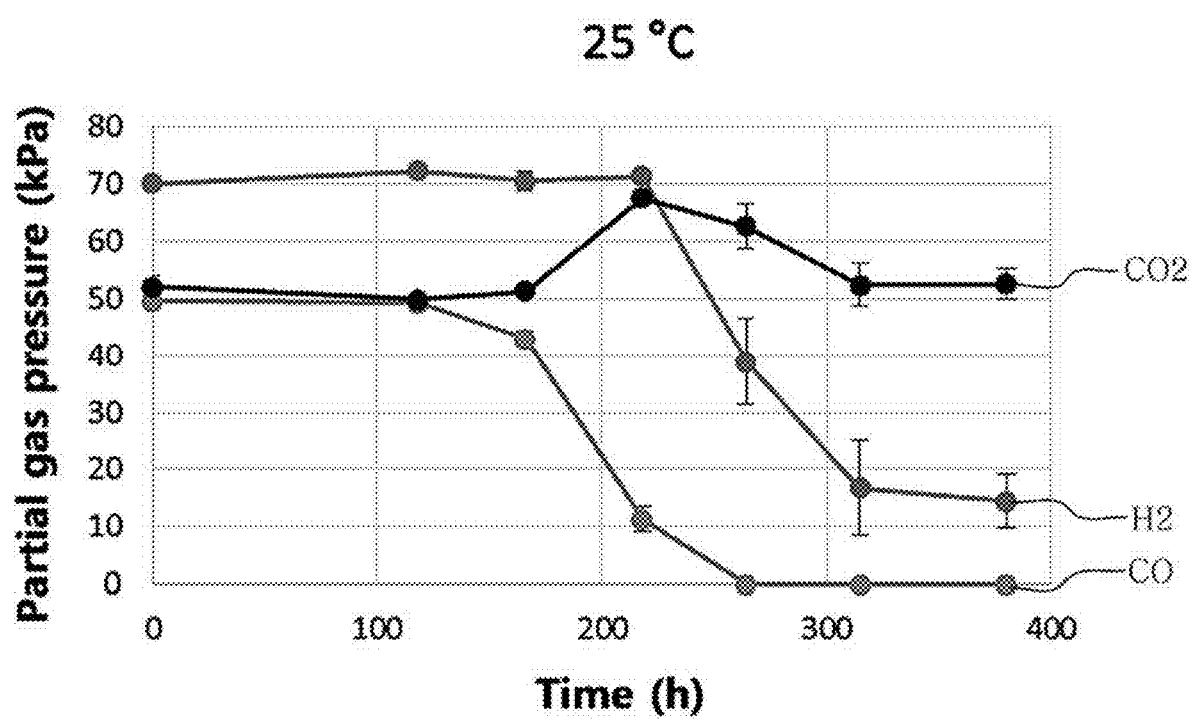
FIG. 12 is a graph showing changes in partial gas pressures in the culture of *Clostridium* sp. JS66 using a gas at the temperature of 25° C. and the concentration of yeast extract in the medium of 1 g/L.
Figure 13:
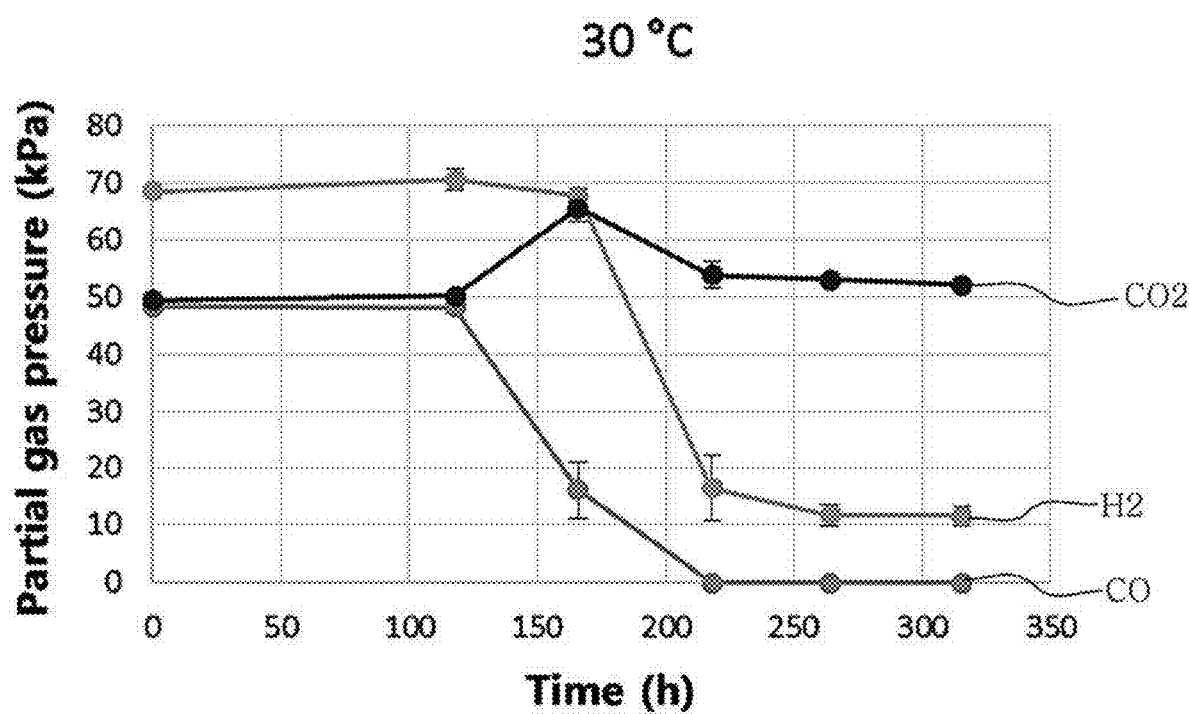
FIG. 13 is a graph showing changes in partial gas pressures in the culture of *Clostridium* sp. JS66 using a gas at the temperature of 30° C. and the concentration of yeast extract in the medium of 1 g/L.
Figure 14:
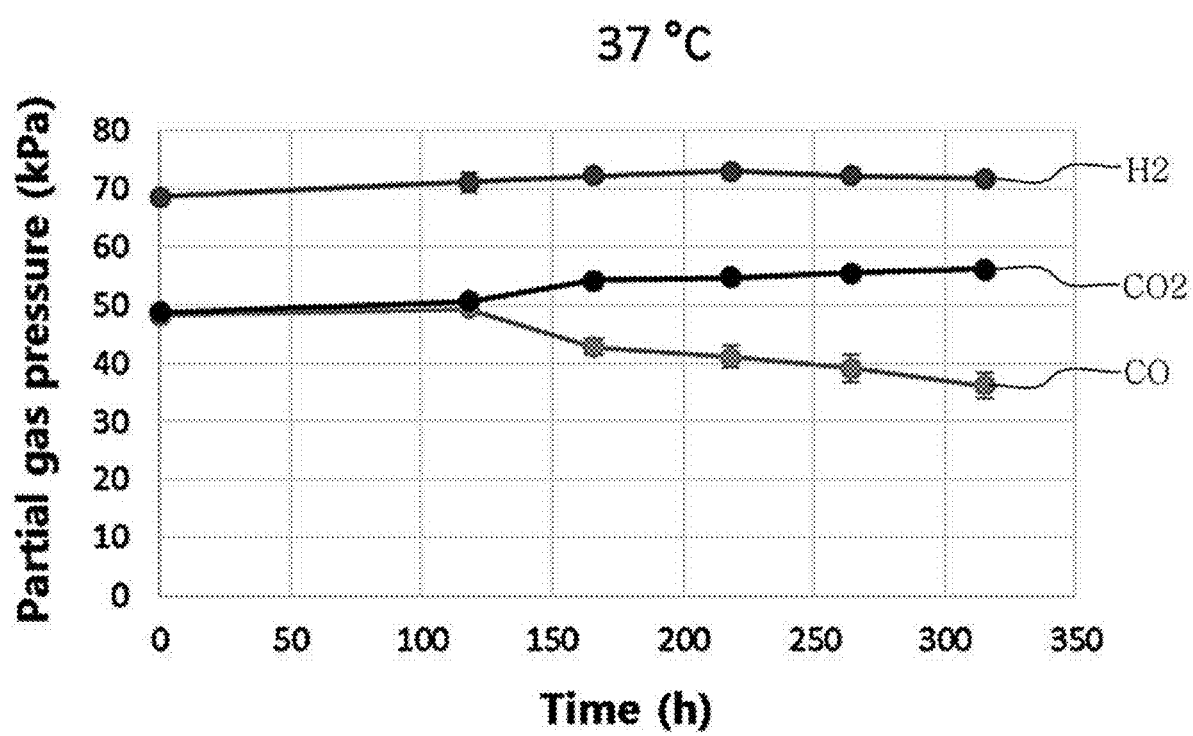
FIG. 14 is a graph showing changes in partial gas pressures in the culture of *Clostridium* sp. JS66 using a gas at the temperature of 37° C. and the concentration of yeast extract in the medium of 1 g/L.

Table 4 and FIG. 10 each show the results of production of metabolites and hexanoic acid depending on the concentration of yeast extract in the medium used. According to the results of experiments with varying the yeast extract concentration, the growth of the strain was the slowest when the concentration of yeast extract was 0.5 g/L and the growth of the strain was similar between the case where the concentration was 1 g/L and the case where the concentration was 2 g/L. Also, when the yeast extract concentration was 1 g/L, the yield of hexanoic acid was 0.04 g/g CO, which was higher than the yield of 0.02 g/g CO at the yeast extract concentration of 2 g/L.

Test Example 5: Growth and Metabolite Production of *Clostridium* sp. JS66 Strain Depending on the Culture Temperature

*Clostridium* sp. JS66 strain was cultured at the concentration of yeast extract in the medium of Table 1 and Table 2 of 1 g/L under the conditions of Test Example 3, with varying the culture temperature of the strain as shown in Table 5 below. Changes in the growth of the strain, partial gas pressures, and the yield of metabolites having at least 4 carbon atoms were identified, and the results are shown in FIG. 11 to FIG. 15 and Table 5.

TABLE 5

| Culture temperature (° C.) | 25 | 30 | 37 |
|---|---|---|---|
| Time at the maximum concentration of hexanoic acid (hour) | 380 | 218 | — |
| pH at the maximum concentration of hexanoic acid | 4.52 | 4.50 | — |
| OD 600 nm value at the maximum concentration of hexanoic acid | 0.85 | 0.99 | — |
| Maximum concentration of hexanoic acid (g/L) | 0.32 | 0.20 | nd |
| Acetic acid (g/L) | 2.31 | 2.11 | — |
| Butyric acid (g/L) | 0.73 | 0.6 | — |
| Ethanol (g/L) | 0.27 | 0.34 | — |

TABLE 5-continued

| Butanol (g/L) | 0.07 | 0.09 | — |
|---|---|---|---|
| Hexanol (g/L) | nd | 0.02 | — |
| Yield of hexanoic acid (g/g CO) | 0.07 | 0.05 | — |

Figure 15:
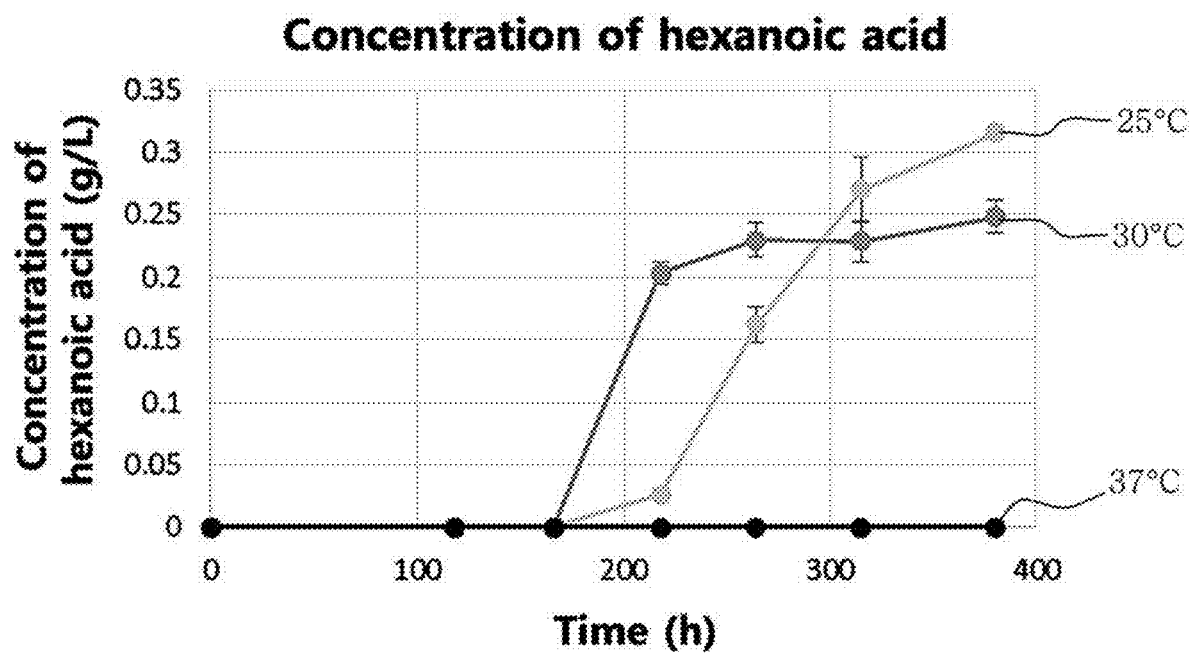
FIG. 15 is a graph showing changes in the yield of hexanoic acid in the culture of *Clostridium* sp. JS66 using a gas at temperatures of 25° C., 30° C., and 37° C. and the concentration of yeast extract in the medium of 1 g/L.

Table 5 and FIG. 15 show the results of production of hexanoic acid depending on the culture temperature. According to the results of experiments with varying the culture temperature, the growth of the strain was the fastest at 30° C. At 25° C., the growth of the strain was slower than that at 30° C., but the maximum concentration of hexanoic acid was higher. At 37° C., the strain did not grow well and hexanoic acid was not produced.

Test Example 6: Growth and Metabolite Production of *Clostridium* sp. JS66 Strain Depending on the Ratio of the Mixed Gas

Figure 16:
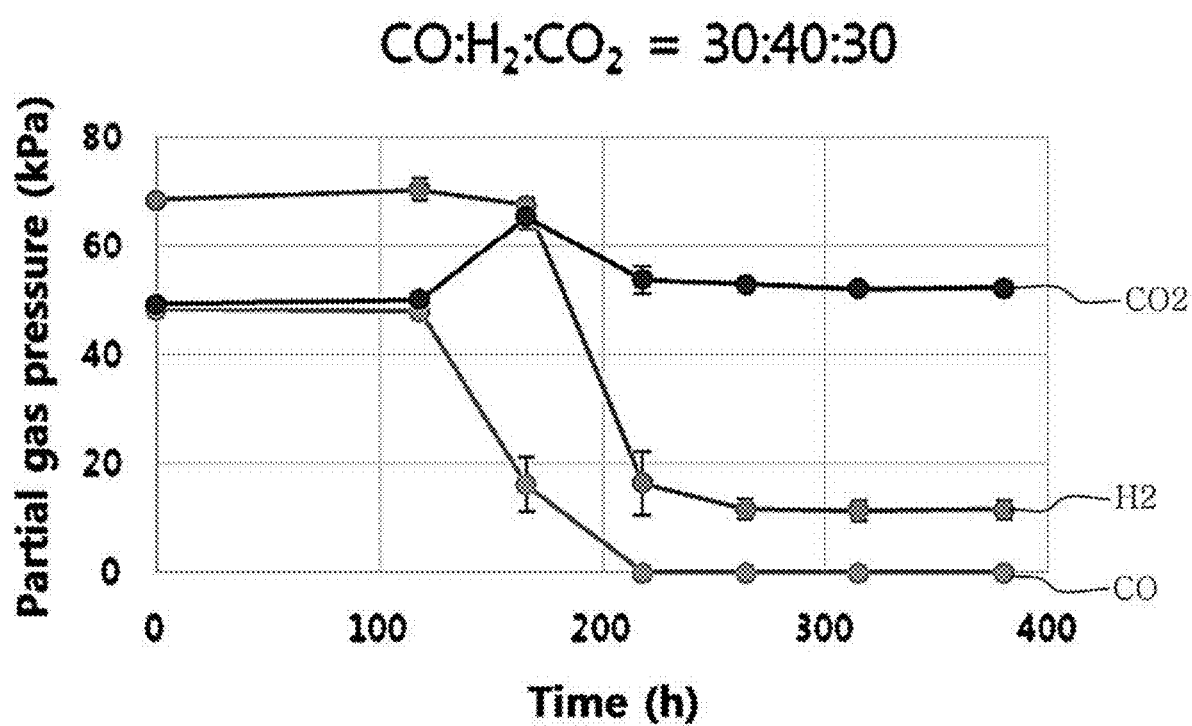
FIG. 16 is a graph showing changes in partial gas pressures in the culture of *Clostridium* sp. JS66 using a mixed gas comprising carbon monoxide, carbon dioxide, and hydrogen at a volume ratio of 30:30:40.
Figure 17:
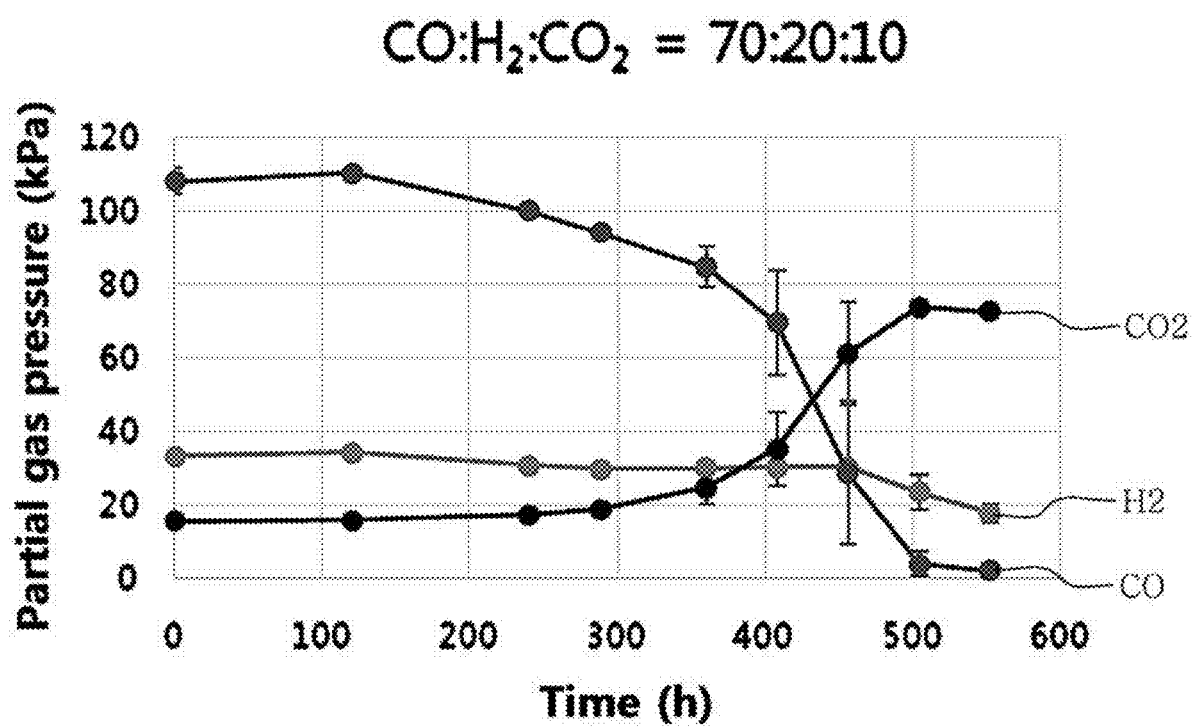
FIG. 17 is a graph showing changes in partial gas pressures in the culture of *Clostridium* sp. JS66 using a mixed gas comprising carbon monoxide, carbon dioxide, and hydrogen at a volume ratio of 70:10:20.

*Clostridium* sp. JS66 strain was cultured at 30° C. and the concentration of yeast extract in the medium of Table 1 and Table 2 of 1 g/L under the conditions of Test Example 3, on an experimental group (Example 1) in which the volume percentages of carbon monoxide, carbon dioxide, and hydrogen in the mixed gas was 30%, 30%, and 40%, respectively, and an experimental group (Example 2) in which the volume percentages of carbon monoxide, carbon dioxide, and hydrogen in the mixed gas was 70%, 10%, and 20%, respectively. Changes in the growth of the strain, partial gas pressures, and the yield of metabolites were identified, and the results are shown in FIG. 16, FIG. 17 and Table 6 below.

TABLE 6

| | Experimental group | |
|---|---|---|
| | Example 1 | Example 2 |
| Volume ratio of the mixed gas ($CO:CO_2:H_2$) | 30:30:40 | 70:10:20 |
| Time at the maximum concentration of hexanoic acid (hour) | 218 | 552 |
| pH at the maximum concentration of hexanoic acid | 4.5 | 4.58 |
| OD 600 nm value at the maximum concentration of hexanoic acid | 0.99 | 1.04 |
| Maximum concentration of hexanoic acid | 0.2 | 0.54 |
| Acetic acid (g/L) | 2.11 | 1.45 |
| Butyric acid (g/L) | 0.6 | 0.57 |
| Ethanol (g/L) | 0.34 | 0.42 |
| Butanol (g/L) | 0.09 | 0.34 |
| Hexanol (g/L) | 0.02 | 0.43 |
| Yield of hexanoic acid (g/g CO) | 0.05 | 0.04 |

The results of Table 6 show that the concentration of hexanoic acid of Example 2 was 0.54 g/L, which was higher than 0.20 g/L of Example 1, but that the yield of Example 1 was 0.05 g/g CO, which was higher than 0.04 g/g CO of Example 2. The growth of bacteria was faster in Example 1 than in Example 2.

Test Example 7: Comparison of the Yield of Metabolites Between *Clostridium* sp. JS66 and *Clostridium carboxidivorans*

*Clostridium* sp. JS66 strain and *Clostridium carboxidivorans* strain (DSM-15243, DSMZ) were cultivated at 30° C. in the same culture medium as the medium of Table 1 and Table 2 of Test Example 3 with the same composition and the same mixed gas conditions as those of Test Example 3 except that the yeast extract concentration was 1 g/L. The concentration of the produced metabolites and the yield of hexanoic acid are shown in Table 7 and FIG.

TABLE 7

| Used strain | Clostridium carboxidivorans | Clostridium sp. JS66 |
|---|---|---|
| pH at the maximum concentration of hexanoic acid | 4.67 | 4.5 |
| OD 600 nm value at the maximum concentration of hexanoic acid | 1.07 | 0.99 |
| Maximum concentration of hexanoic acid (g/L) | 0.05 | 0.25 |
| Acetic acid (g/L) | 2.67 | 2.11 |
| Butyric acid (g/L) | 0.17 | 0.60 |
| Ethanol (g/L) | 0.67 | 0.34 |
| Butanol (g/L) | 0.07 | 0.09 |
| Hexanol (g/L) | nd | 0.02 |
| Yield of hexanoic acid (g/g CO) | 0.01 | 0.05 |

Figure 18:
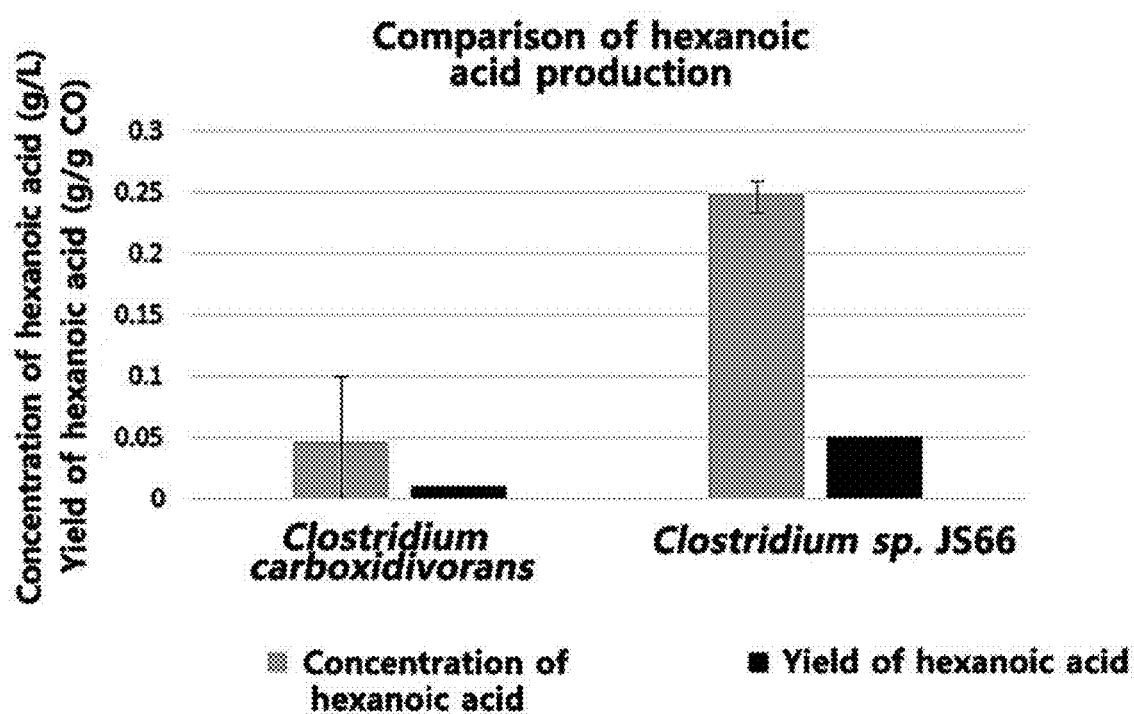
FIG. 18 is a graph showing the concentration and yield of the hexanoic acid produced from each of *Clostridium* sp. JS66 and *Clostridium carboxidivorans* when using the same medium and a mixed gas with the same composition of carbon monoxide, carbon dioxide, and hydrogen.
Figure 19:
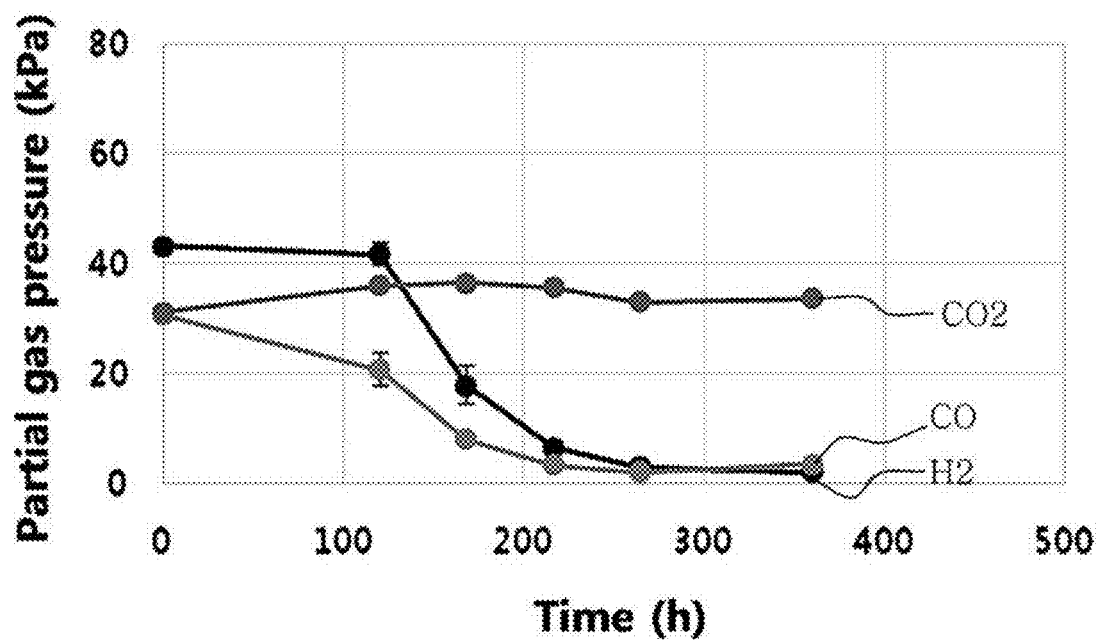
FIG. 19 is a graph showing changes in partial gas pressures in the culture of *Clostridium* sp. JS66 using a gas at the total pressure of a mixed gas of carbon monoxide, carbon dioxide, and hydrogen of 100 kPa.
Figure 20:
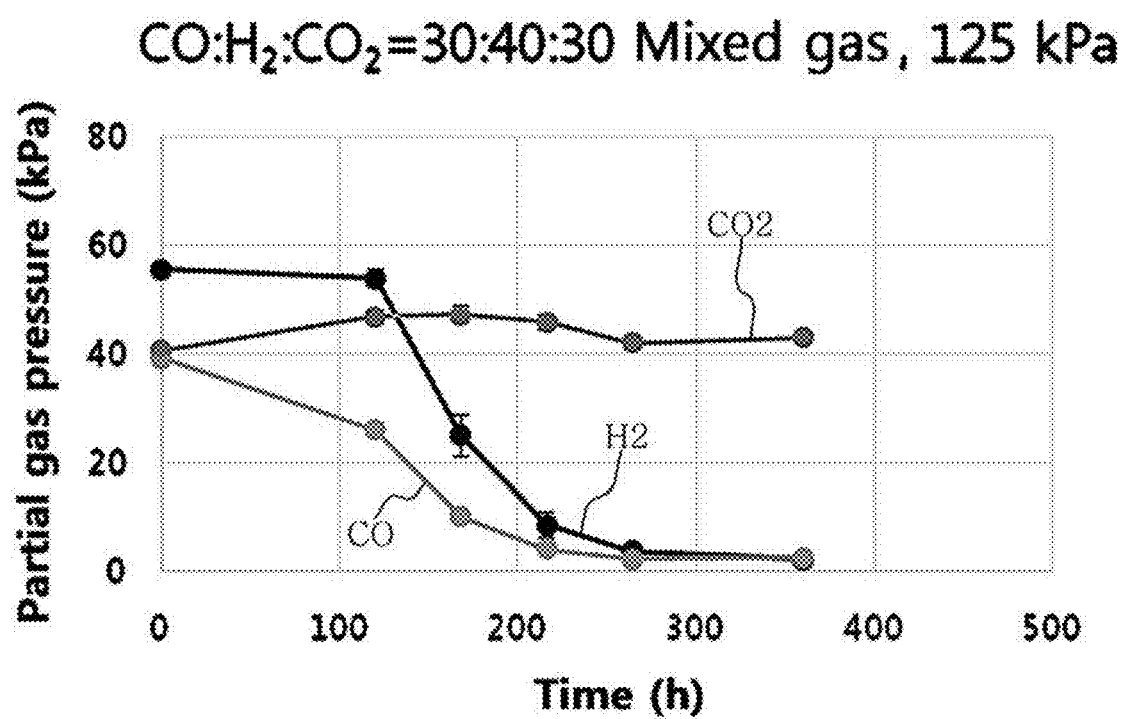
FIG. 20 is a graph showing changes in partial gas pressures in the culture of *Clostridium* sp. JS66 using a gas at the total pressure of a mixed gas of carbon monoxide, carbon dioxide, and hydrogen of 125 kPa.
Figure 21:
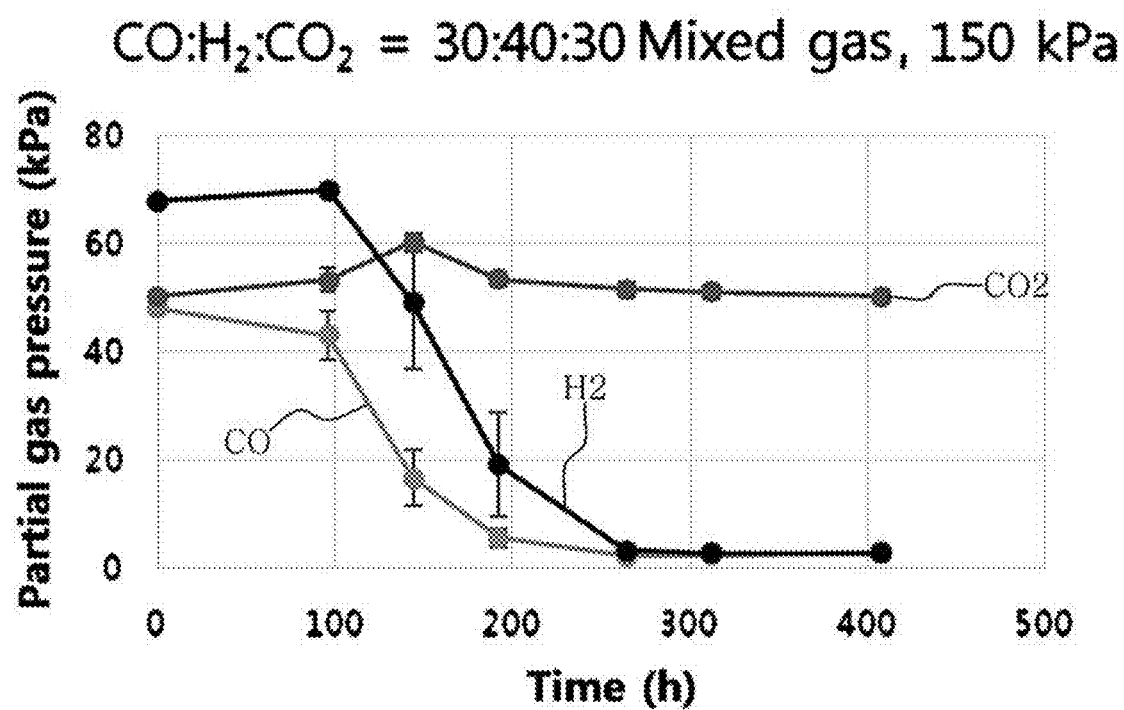
FIG. 21 is a graph showing changes in partial gas pressures in the culture of *Clostridium* sp. JS66 using a gas at the total pressure of a mixed gas of carbon monoxide, carbon dioxide, and hydrogen of 150 kPa.
Figure 22:
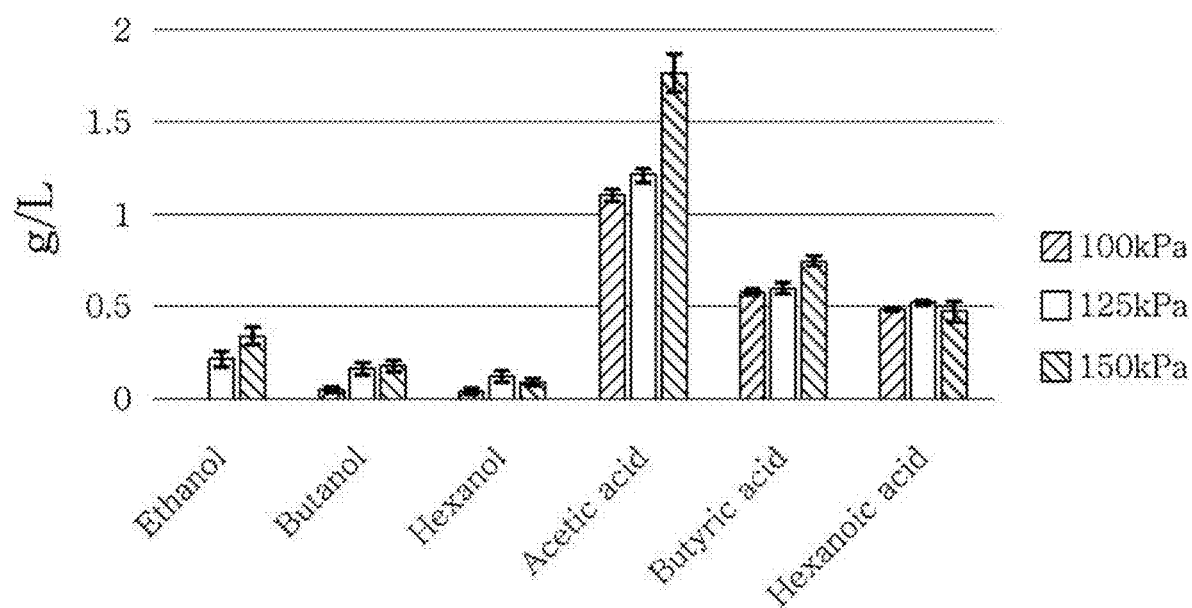
FIG. 22 is a graph comparing the concentrations of metabolites with varying the total pressure of the mixed gas.

Table 7 and FIG. 18 each show the results of production of metabolites and hexanoic acid of *Clostridium* sp. JS66 and *Clostridium carboxidivorans* when the same mixed gas of carbon monoxide, carbon dioxide, and hydrogen and the same medium were used. The maximum concentration of hexanoic acid was higher in *Clostridium* sp. JS66, and accordingly, the yield of hexanoic acid was also significantly higher in *Clostridium* sp. JS66, which exhibited the yield of hexanoic acid of 0.05 g/g CO, which was 5 times higher than 0.01 g/g CO of the reference strain *Clostridium carboxidivorans*.

Test Example 8: Comparison of the Growth and Metabolite Production of *Clostridium* sp. JS66 with Varying the Gas Pressure

*Clostridium* sp. JS66 strain was cultured under the conditions of Test Example 3, the medium composition of Table 1 and Table 2, and the yeast extract concentration of 1 g/L. The volume percentages of carbon monoxide, carbon dioxide, and hydrogen in the mixed gas was 30%, 30% and 40%, respectively. At the stirring rate of 100 rpm, the total pressure of the mixed gas was varied from 100 kPa (=1 bar) to 125 kPa (=1.25 bar) and 150 kPa (=1.5 bar). The metabolites and the yield were identified, and the results are shown in FIG. 19 to FIG. 22 and Table 8 below.

TABLE 8

| Total pressure of the mixed gas (kPa) | 100 | 125 | 150 |
|---|---|---|---|
| Time at the maximum concentration of hexanoic acid (hour) | 360 | 360 | 408 |
| Maximum concentration of hexanoic acid (g/L) | 0.49 | 0.52 | 0.47 |
| Acetic acid (g/L) | 1.1 | 1.21 | 1.76 |
| Butyric acid (g/L) | 0.57 | 0.6 | 0.74 |
| Ethanol (g/L) | 0 | 0.21 | 0.34 |
| Butanol (g/L) | 0.05 | 0.16 | 0.18 |
| Hexanol (g/L) | 0.04 | 0.12 | 0.09 |
| Yield of hexanoic acid (g/g CO) | 0.19 | 0.15 | 0.1 |

The results of Table 8 show that the concentration and yield of hexanoic acid were 0.49 g/L and 0.19 g/g CO at 100 kPa, 0.52 g/L and 0.15 g/g CO at 125 kPa, and 0.47 g/L and 0.10 g/g CO at 150 kPa. As the total pressure of the mixed gas decreased from 150 kPa to 100 kPa, the concentration of acetic acid, butyric acid, ethanol, butanol and hexanol decreased with the concentration of the hexanoic acid produced maintained at a similar level, resulting in the increased yield of hexanoic acid.

From the results of the test examples, it can be understood that the isolated strain *Clostridium* sp. JS66 can use a mixed gas of carbon monoxide, carbon dioxide, and hydrogen as a substrate under anaerobic conditions and produces metabolites having at least 4 carbon atoms, butyric acid, butanol, hexanoic acid, and hexanol, as metabolites. All of the carbon monoxide used in the experiments was consumed, which shows that carbon monoxide as a gas substrate was not sufficiently supplied. That is, it cannot be considered that the experiments were performed under optimal conditions for production of a maximum amount of hexanoic acid. Nevertheless, the strain produced hexanoic acid and butyric acid at a higher yield than the conventional *Clostridium carboxidivorans* strain. Therefore, if the present invention is applied to fermentor experiments capable of supplying an additional mixed gas or continuously supplying a mixed gas, hexanoic acid and butyric acid will be produced at a higher yield than that shown in these test examples.

In one aspect, the present invention provides a novel *Clostridium* sp. strain producing metabolites having 6 carbon atoms in a significantly higher yield than conventional strains.

In one aspect, the present invention provides a novel *Clostridium* sp. strain producing metabolites having 6 carbon atoms in a high yield not only in sugar-based metabolism but also when a carbon source other than sugars is used as a substrate.

In another aspect, the present invention provides a novel *Clostridium* sp. strain producing metabolites having 6 carbon atoms in a high yield using a gas comprising at least one of carbon monoxide and carbon dioxide as a substrate.

In another aspect, the present invention provides a method for producing metabolites having at least 4 carbon atoms using the novel strain.

In another aspect, the present invention provides a method for producing metabolites having at least 4 carbon atoms using a mixed gas comprising at least one of carbon monoxide and carbon dioxide as a substrate.

In another aspect, the present invention provides a method for producing metabolites having 6 carbon atoms in a high yield.

In another aspect, the present invention provides a method for producing metabolites having at least 4 carbon atoms while reducing the production of acetic acid and ethanol as by-products in the production of metabolites using microorganisms.

In another aspect, the present invention allows to reduce the production of by-products generated when conventionally producing hexanoic acid using a mixed gas comprising carbon monoxide and carbon dioxide as a substrate.

In another aspect, the present invention provides an eco-friendly method for producing hexanoic acid which allows to fix greenhouse gases, steelworks by-product gases (including CO, $CO_2$ and $H_2$), and syngases while producing useful compounds.

While the present invention has been described with respect to the specific embodiments, it will be apparent to those skilled in the art that various changes and modifications may be made without departing from the spirit and scope of the invention as defined in the following claims.

Accession Number
Depository authority: Korea Research Institute of Bioscience and Biotechnology
Accession number: KCTC13355BP
Deposit date: 20170919

What is claimed is:

1. A medium composition comprising:
a *Clostridium* sp. JS66 strain of accession No. KCTC13355BP producing metabolites having 4 to 6 carbon atoms; and
an effective amount of a substrate for production of said metabolites;
wherein said substrate comprises:
   carbon monoxide and carbon dioxide;
   glucose; and
   at least one sugar-based carbon source of fructose, galactose, xylose, arabinose, mannose, cellobiose, and sucrose; and
wherein said metabolites comprise:
   hexanoic acid; and
   at least one of butyric acid, butanol and hexanol.

2. The medium composition according to claim 1,
wherein the metabolites further comprise at least one of butyric acid and hexanol.

3. The medium composition according to claim 1,
wherein the *Clostridium* sp. strain produces the metabolites using the substrate, wherein said substrate comprises:
glucose and at least one sugar-based carbon source of galactose, xylose, arabinose, mannose, cellobiose, and sucrose.

4. The medium composition according to claim 1,
wherein the *Clostridium* sp. strain produces the metabolites using a mixed gas further comprising hydrogen and of said carbon monoxide and carbon dioxide.

5. The medium composition according to claim 1,
wherein the optimal culture temperature is 25° C. to 30° C.

6. A method for producing metabolites having 4 to 6 carbon atoms, comprising supplying *Clostridium* sp. JS66 strain, thereby producing said metabolites of accession No. KCTC13355BP to a substrate comprising a carbon source and culturing the strain.

7. The method for production according to claim 6,
wherein the culture is carried out at 25° C. to 30° C.

8. The method for production according to claim 6,
wherein the culture is carried out at pH 5 to pH 8.

9. The method for production according to claim 6,
wherein the culture is carried out under anaerobic conditions.

10. The method for production according to claim 6,
wherein the substrate comprises at least one of glucose, fructose, galactose, xylose, arabinose, mannose, cellobiose, and sucrose.

11. The method for production according to claim 6,
wherein the substrate comprises at least one of carbon monoxide and carbon dioxide.

12. The method for production according to claim 11,
wherein the substrate further comprises hydrogen.

13. The method for production according to claim 11,
wherein the culture is carried out at a total gas pressure of 3 bar or less.

14. The method for production according to claim 6,
wherein the culture is carried out in a medium containing yeast extract.

15. The method for production according to claim 14,
wherein the medium contains 0.1 g/L to 10 g/L of yeast extract.

16. A method for fixing carbon monoxide and carbon dioxide, comprising supplying a mixed gas comprising carbon monoxide and carbon dioxide to a culture of *Clostridium* sp. JS66 strain of accession No. KCTC13355BP and culturing said strain, thereby fixing said carbon monoxide and carbon dioxide.

17. The method for fixing carbon monoxide and carbon dioxide according to claim 16, further comprising producing metabolites having 4 to 6 carbon atoms from carbon monoxide and carbon dioxide.

* * * * *